United States Patent

Naef et al.

[11] Patent Number: 4,701,543
[45] Date of Patent: Oct. 20, 1987

[54] PROCESS FOR THE PREPARATION OF OXYGENATED DECALINE DERIVATIVES

[75] Inventors: Ferdinand Naef, Carouge; Christian Vial, Le Lignon, both of Switzerland

[73] Assignee: Firmenich S.A., Geneva, Switzerland

[21] Appl. No.: 886,845

[22] Filed: Jul. 18, 1986

[30] Foreign Application Priority Data

Aug. 12, 1985 [CH] Switzerland ............ 3445/85

[51] Int. Cl.$^4$ ............................................ C07D 307/92
[52] U.S. Cl. .................................. 549/458; 562/501; 568/445; 568/819
[58] Field of Search .................. 562/501; 568/445; 549/458

[56] References Cited

PUBLICATIONS

Rao et al., J. Org. Chem. 44, pp. 456–458, (1979).
Wallace et al., J. Org. Chem. 30, pp. 3768–3771 (1965).
Demole et al., Helv. Chim. Acta, 50, pp. 1314–1321 (1967).

Primary Examiner—Henry R. Jiles
Assistant Examiner—Bernard I. Dentz
Attorney, Agent, or Firm—Pennie & Edmonds

[57] ABSTRACT

Oxygenated decaline derivatives of formula

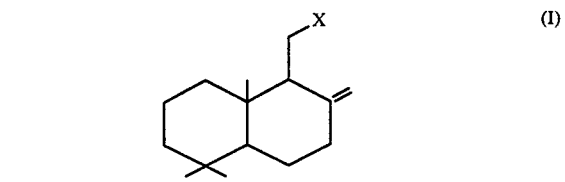

wherein X represents a COOH or a CHO group are obtained according to a process which consists in the oxidation of a ketone of formula

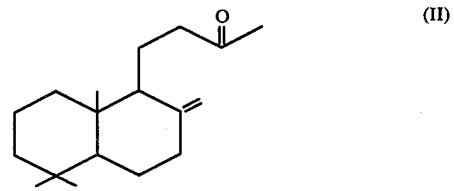

by means of oxygen in a basic medium constituted by potassium tert-butoxide in 1,2-dimethoxyethane.

Compounds (I) are useful starting materials for the preparation of AMBROX ® (registered tradename of Firmenich SA, Geneva, Switzerland) which is an ingredient in perfumes.

4 Claims, No Drawings

PROCESS FOR THE PREPARATION OF OXYGENATED DECALINE DERIVATIVES

BRIEF SUMMARY OF THE INVENTION

This invention relates to a new process for the preparation of useful intermediates for the synthesis of AMBROX ® (registered tradename of Firmenich SA, Geneva, Switzerland) or 3a,6,6,9a-tetramethylperhydronaphto[2,1-b]furan. It relates in particular to the preparation of oxygenated decaline derivatives of formula

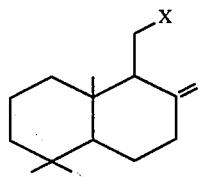

(I)

wherein X represents a COOH or a CHO group. The process of the invention consists in the oxidation of a ketone of formula

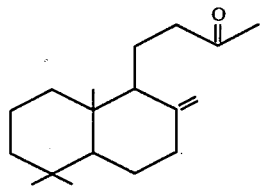

(II)

by means of oxygen in a basic medium constituted by potassium tert-butoxide in 1,2-dimethoxyethane.

Conversion of (I) into AMBROX occurs through known techniques via reduction, for example by means of LiAlH$_4$, followed by acidic cyclisation.

BACKGROUND OF THE INVENTION

AMBROX ® (registered tradename of Firmenich SA, Geneva, Switzerland) or 3a,6,6,9a-tetramethylperhydronaphto[2,1-b]furan is one of the ingredients of choice in a great variety of perfuming compositions. Its characteristic odor of ambergris possesses a special power of diffusiveness which has remained so far unmatched. Since its discovery [see Helv. Chim. Acta 33, 1251 (1950)] numerous syntheses for its preparation have been proposed by different research groups. These utilise the oxidative degradation technic on diterpenes such as sclareol or manool, or use ambreine as starting material [G. Ohloff in Fragrance Chemistry, Ed. Ernst T. Theimer, p. 545, Academic Press (1982)].

Among the compounds having a structure analogous to that of AMBROX, the following oxygenated decalinic aldehydes have been described in the prior art

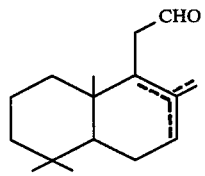

wherein the dotted lines represent an additional double bond [see British Pat. No. 701,911 and West-German Pat. No. 1,019,031 and Parfümerie and Kosmetik 54, 335 (1973)]. Very appreciated for their ambergris fragrance, these compounds represent not only useful perfuming ingredients but also they have a utility as intermediates for the preparation of AMBROX.

In effect, the said aldehydes together with the corresponding acids can be reduced to their corresponding carbinols, e.g. by treatment with LiAlH$_4$, which carbinols through acidic cyclisation give the desired AMBROX according to the following reaction pathway:

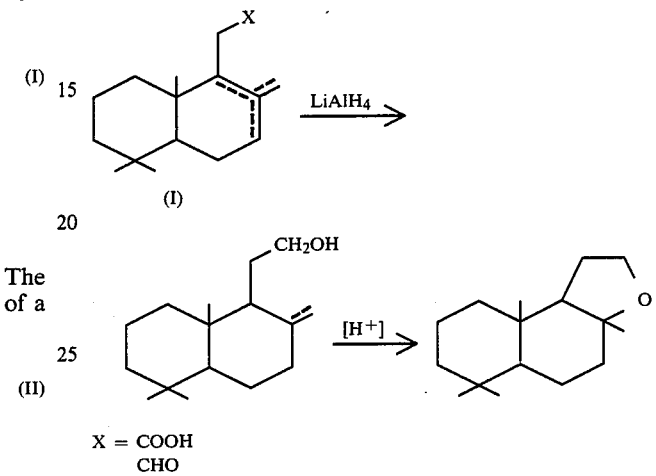

X = COOH
CHO

The oxygenated decaline derivatives of formula (I) have been obtained in the past by processes [see above mentioned references] which in actual experience are uneconomical either because they do not enable the preparation of the desired end-product in useful yields or because they use polluting reactants or non easily available products.

THE INVENTION

We have now discovered that the compounds of formula (I), especially those possessing an exocyclic double bond in the gamma-position, could be obtained by means of an original process characterized in that a ketone of formula

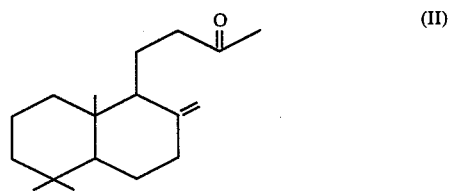

(II)

is oxidized by means of oxygen in a basic medium. This type of oxidation is analogous in a way to the conversion of cyclic ketones into their dicarboxylic acid derivatives [see in this respect: D. V. Rao et al., J. Org. Chem. 44, 456 (1979) and T. S. Wallace et al., J. Org. Chem. 30, 3768 (1965)]. The process of the invention is characterized in that the oxidation is carried out in a basic medium constituted by potassium tert-butoxide in solution in 1,2-dimethoxyethane.

The product thus obtained occurs under the form of a mixture containing practically equivalent parts of the aldehyde of formula

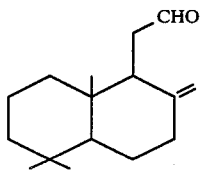

and the acid of formula

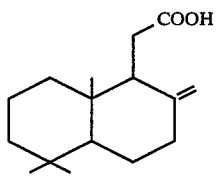

This mixture is used directly for the following conversion into AMBROX according to the method illustrated by the above given reaction scheme.

The reaction which characterizes the process of the invention is effected preferably at a controlled temperature of between about 0° and +20° C. According to a mode of operation, the starting ketone in solution in 1,2-dimethoxyethane, is added to a cooled mixture of potassium tert-butoxide, also dissolved in 1,2-dimethoxyethane, then when the reaction mixture has reached a temperature of about +10° C., a flow of oxygen is passed through the solution. Alternatively, the operation occurs in a pressurized closed vessel under an oxygen atmosphere. The absorption of oxygen is accompanied by the warming up of the mixture and the temperature has to be kept under +20° by applying an external cooling.

The mixture of the desired aldehyde and acid can then be separated from the reaction mixture by extraction with an organic solvent, e.g. by means of diethyl ether.

Ketone (II) used as starting material for the process of the invention can be obtained according to the process described by A. K. Dey and H. R. Wolf [Helv. Chim. Acta 61, 1004 (1978)] starting from eperuic acid. It can also be prepared from manool as indicated by E. Demole et H. Wuest [Helv. Chim. Acta 50, 1314 (1967)].

The invention is better illustrated by the following example wherein the temperatures are indicated in degrees centigrade and the abbreviations have the meaning common in the art.

EXAMPLE 150 ml of anhydrous 1,2-dimethoxyethane (filtered on basic $Al_2O_3$ and kept on 4 Å Linde) and 26.9 g (0.24 mole) of potassium tert-butoxide were added in a 500 ml vessel equipped with a septum, a thermometer and a tube enable to set the apparatus under oxygen. The mixture was cooled to 5° (ice-bath) and while stirring 15.72 g (0.06 Mole) of 15,16-dinorlabd-8(20)-en-13-one in 20 ml of anhydrous 1,2-dimethoxyethane were added through a sirynge. As soon as the temperature has reached 10°, the mixture is stopped, the vessel is purged with dry oxygen, hermetically closed and set under oxygen stream while the stirring is put on again. The oxygen absorption begins immediately (exothermic) and after 25 minutes at a temperature of between about 10° and 16° (ice-bath) 2.75 l of oxygen had been absorped and a clear slow down of the reaction was observed. The ice-bath was removed and the temperature was increased 20°-25° while the stirring was kept for 1 h and 35 minutes. In this way, 1.55 l of oxygen was further absorbed bringing the total oxygen uptake to 4.3 l. The reaction mixture was poured onto ice, acidified with an icy 10% HCl solution, extracted twice with diethyl ether, washed until neutrality with a NaCl solution, dried over $Na_2SO_4$ and finally concentrated.

17.9 g of a material were thus obtained, 100 mg of which were treated with diazomethane for separation on gas phase chromatography (SP 1000 5% on Chromosorb W 80-100 mesh, 2.5 m, isoth. 240°).

It was thus determined that the obtained product consisted in a mixture of 40% of 13,14,15,16-tetranorlabd-8(20)-en-12-al [identical to a sample prepared according to the process described in the literature (see G. Ohloff, E. Theimer, Ed. Academic Press 1982, p. 535 and references cited therein)].

IR (film): 3180, 2940, 2720, 1730, 1650, 1470, 1160, 905 $cm^{-1}$;

$H^1$-RMN (60 MHz, $CDCl_3$): 0.70; 0.82; 0.90 (3s, 3H); 4.35 and 4.77 (2s broad, 2H); 9.55 (t: J=2 Hz, 1H) δ ppm.

The aldehyde was accompanied by 13,14,15,16-tetrarnorlabd-8(20)-en-12-oic acid in an amount of 45% as identified by its methyl ester which possessed the following analytical characters:

IR (film): 2950, 1745, 1650, 1470, 1440, 1170, 900 $cm^{-1}$;

$H^1$-RMN (60 MHz, $CDCl_3$): 0.70; 0.81; 0.89 (3s, 3H); 3.60 (s, 3H); 4.45 and 4.72 (2s, broad, 2H) δ ppm.

15,16-Dinorlabd-8(20)-en-13-one used as starting material in the above described process was prepared by oxidation with potassium permanganate of (+)-manool according to the procedure described by E. Demole and H. Wuest [Helv. Chim. Acta 50, 1314 (1967)].

The conversion of the mixture of the obtained aldehyde and acid into AMBROX is carried out by reduction with $LiAlH_4$ in diethyl ether solution and cyclisation of the resulting carbinol, or 13,14,15,16-tetranorlabd-8(20)-en-12-ol, with an acidic cyclising agent.

What we claim is:

1. Process for the preparation of oxygenated decaline derivatives of formula

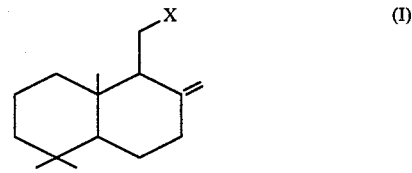

wherein symbol X represents a COOH or a CHO radical, which comprises oxidizing a ketone of formula

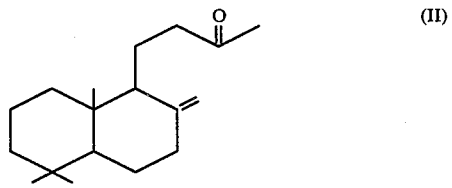

by means of oxygen in a basic medium constituted by potassium tert-butoxide in solution in 1,2-dimethoxyethane.

2. Process according to claim 1, wherein the reaction is carried out at a temperature of between about 0° and +20° C.

3. Process according to claim 1, wherein the reaction is carried out at atmospheric pressure or at a pressure slightly above the atmospheric pressure.

4. Process for the conversion of the product obtained according to claim 1 into 3a,6,6,9a-tetramethylperhydronaphtho[2,1-b]furan by reducing it with a metal hydride to give a carbinol of formula

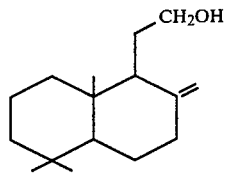

and cyclizing the said carbinol by means of an acidic cyclization agent.

* * * * *